United States Patent [19]
Faust

[11] Patent Number: 4,469,227
[45] Date of Patent: Sep. 4, 1984

[54] PACKAGE FOR CRYOGENICALLY FROZEN LIQUIDS

[76] Inventor: Clifford Faust, 4316 St. Charles Rd., Bellwood, Ill. 60104

[21] Appl. No.: 524,100

[22] Filed: Aug. 17, 1983

[51] Int. Cl.³ ............... B65D 30/10; B65D 33/00; B65B 63/08; F25D 3/08
[52] U.S. Cl. .................................. 206/527; 62/60; 62/293; 206/526; 383/119; 248/95
[58] Field of Search ............ 206/527, 525; 62/60, 62/293; 383/119, 901; 298/95

[56] References Cited

U.S. PATENT DOCUMENTS

| | | | |
|---|---|---|---|
| 2,260,450 | 10/1941 | Guinane | 62/60 |
| 2,964,920 | 12/1960 | Staebler | 62/60 |
| 2,966,041 | 12/1960 | Zearfoss, Jr. et al. | 62/60 |
| 3,875,754 | 4/1975 | Faust et al. | 62/60 |
| 3,952,536 | 4/1976 | Faust et al. | 62/293 |
| 4,194,369 | 3/1980 | Faust et al. | 62/60 |
| 4,251,995 | 2/1981 | Pert et al. | 62/60 |

Primary Examiner—William T. Dixson, Jr.
Attorney, Agent, or Firm—John H. Shurtleff

[57] ABSTRACT

A package for a cryogenically frozen liquid material which includes an enclosed flat pouch formed by two layers of a cryogenically durable, transparent, thermoplastic polymer film having heat-sealed inner edges with laminated fins extending outwardly along at least about 15% of the pouch periphery, the fins being extensions of the 2 film layers and having a heat-sealed area along their inner edges, and also at least in a marginal area adjacent their outermost peripheral edge. The invention also includes a protective supporting package to enclose and securely hold the pouch and its contents.

20 Claims, 16 Drawing Figures

PACKAGE FOR CRYOGENICALLY FROZEN LIQUIDS

BACKGROUND OF THE INVENTION

This invention relates to an improved package for cryogenically frozen liquid materials, especially in the preservation of valuable biological liquids such as human blood, bone marrow or components thereof. More particularly, the present invention is directed to an improved flexible, slack-fillable, transparent, flat plastic pouch which is readily sterilized and which is capable of being protected against leakage, contamination or other damage by combination with a metal enclosure or retainer comprising parallel metal retaining plates and means to clamp the pouch in a substantially fixed position between said plates. Flexible flat pouches with relatively uniform thin cross sections have been earlier described in such references as Underwood U.S. Pat. No. 3,576,650, and further refinements and improvements in the apparatus and method of flattening and freezing these liquid filled pouches have been disclosed in my U.S. Pat. No. 3,898,023 as well as U.S. Pat. Nos. 3,875,754 and 3,952,536. All of these references stress the importance of maintaining a uniform cross section as the liquid is frozen at cryogenic temperatures so as to permit the carefully controlled rapid freeze and thaw rates needed to prevent damage to the cells or other components of the biological material. It is further noted that this object is more easily achieved by the use of thin, rigid stainless steel liquid containers in place of plastic pouches or bags, but the use of such steel containers has many other disadvantages including venting problems, lack of transparency to inspect the contents and the inherent difficulty of maintaining sterility of the container and its contents. Moreover, the cost of such steel containers is quite high and they cannot be reused.

On the other hand, flat plastic pouches when used as sterile containers for cryogenically frozen liquids continue to cause problems even when properly filled and rapidly frozen into a thin, relatively uniform cross section free of bubbles and protected between a pair of metal plates. Thus, as noted in U.S. Pat. Nos. 3,952,536 and 3,875,754, it is advisable to protect against drop damage by loading the slack filled pouches transversely into restraining plates, i.e. so that the heat seals along opposite edges of the pouch are arranged parallel to the open sides of the restraining plates and at right angles to their closure returns. Moreover, it was found necessary to fold the heat seals over or under the flattened pouch prior to closing the plates and freezing. While this careful assembly helps to prevent pouch rupture when the frozen package is dropped on a concrete floor, the resulting pouch no longer retains a uniform cross section due to necking down of the pouch at the folds and displacement of liquid contents by the folded over parts, especially by the inlet and outlet ports with their tubular inserts.

The use of ridges or dimples which interrupt the flat plate surfaces in these prior patents was recommended to immobilize or lock the pouch in place, especially when frozen, but again such measures reduce the uniformity of the cross section of the slack filled pouch. And due to the slight flexibility of the restraining plates, such measures alone do not effectively prevent movement of the frozen pouch and rupture of a heat sealed edge if dropped on edge or on a corner.

Another problem in the use of prior metal containers or retainers arises in the handling of the package after it has been frozen at a very low temperature, e.g. on the order of about that of liquid nitrogen (−193° C.). Only a very slight rupture or puncture may occur without immediate detection causing a severe disaster when the biological material is later thawed and placed in use. In general, the metal container or retainer must be carefully handled with special tools or by heavily insulated hands, and in either case, the handling becomes relatively difficult and clumsy so as to increase the probability of accidentally dropping the package and rupturing the frozen pouch. Moreover, it is difficult to grasp the container in order to open or close it carefully when inserting or removing the pouch. It is important to maintain the integrity of the entire package during rapid freezing, storage and subsequent use, and prior packages have not substantially reduced the risk of accidental mishandling and the consequential damage to the package and contamination of the biological material.

SUMMARY OF THE INVENTION

It is therefore a primary object of the present invention to provide an improvement in packages intended for use in cryogenically freezing, storing and handling of frozen liquid materials, especially biological liquids such as blood, blood plasma, bone marrow and the like, whereby damage to the package is substantially completely avoided and unrecognized damage or contamination of the contents can be practically eliminated. Another object of the invention is to provide a package for cryogenically frozen biological liquids which is relatively economical and easy to manufacture even though new and improved functions are added thereto. Yet another object of the invention is to provide a package assembly comprising a plastic pouch and metal retainer plates which will maintain a relatively thin and uniform cross section of the contents of the pouch during freezing. Moreover, this package assembly includes the individually designed pouch and paired set of retainer plates together with means of clamping and supporting the pouch in a substantially fixed position between the plates. Still another object is to provide a metal container which is easily and safely handled under all conditions.

These and other objects and advantages have been accomplished in accordance with the invention, by providing a special construction of a flexible pouch with supporting fins or flaps as extensions beyond the heat-sealed edges of the pouch enclosure and by further providing a metal plate retainer with added clamping means to hold the retainer together while also securing the flexible pouch in its fixed position. In a preferred embodiment, special pivoted clamping means attached to opposing plates of the retainer also act as handles or arm extensions for opening and closing the plates.

THE DRAWINGS

The invention is described in greater detail in the form of certain preferred embodiments as illustrated by the accompanying drawings wherein.

DETAILED DESCRIPTION OF THE INVENTION

Figure 1:
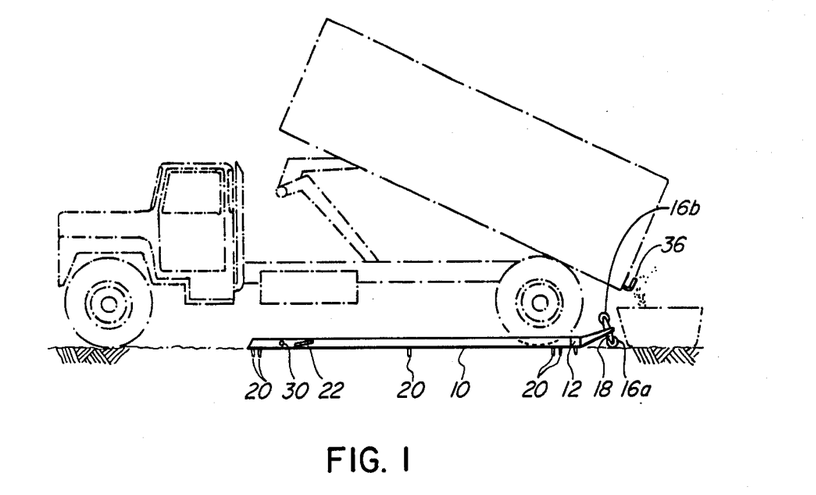
FIG. 1 is a perspective view of a preferred embodiment of the transparent pouch constructed in accordance with the invention with fins on three sides and inlet and outlet ports arranged on the fourth side.

Referring first to FIGS. 1-4, the invention provides a preferred transparent plastic pouch 1 shown in its sealed condition in FIG. 1 after being slack filled according to well known procedures with a liquid biological material 2 such as blood or components thereof. Suitable inlet and outlet ports, as represented by tubular members 3 and 4, are placed at the upper end of the pouch and sealed within narrow tubular segments 5 and 6, respectively, attached to the main body 7 of the pouch enclosure. These ports are helpful in rapidly filling the bag with a liquid under sterile conditions and then maintaining the contents in a sealed condition during freezing and storage. When thawed for subsequent use, one of these ports 4 is opened to withdraw the liquid. The pouch is initially filled through the other port 3 by means of a transfer set spike 8 which provides a standard connection.

The preferred pouch is made of two layers of a biaxially oriented polyethylene which remains relatively flexible and resistant to abrasion and breakage at the very low temperatures required for cryogenic freezing, e.g. below about −193° C. or 80° K., the temperature of liquid nitrogen. In general, transparent thermoplastic polymer films with cryogenic durability are available in the market place, and the polyolefins have been found to be particularly useful for this purpose, especially the oriented polyethylenes. Biaxial orientation is important to provide a high degree of tensile strength in the axial and transverse directions of the polymer film (as viewed in the direction of extrusion of a blown tubular film). The film will retain this strength except in the regions where heat sealing causes a loss of orientation and a corresponding reduction in film strength.

As will be noted in FIG. 1, the main body 7 of the pouch 1 has a substantially rectangular shape as formed by the heat seal 9 which extends from the inlet port 3 along one side 9a, across the bottom 9b, along the opposite side 9c to the outlet port 4, and generally across the top 9d between the two ports. The two tubular members 3 and 4 of the ports can also be made of polyethylene and effectively sealed in place by a double heat seal 10, i.e. the parallel heat seals 10a and 10b which can be applied simultaneously to the circumference of both ports while resealing transversely to the side seals 9a and 9c and the top end seal 9d where all of these pouch seals extend upwardly from the rectangular enclosure 7 to form the port segments 5 and 6. The upper end of segment 5 is closed by the heat seal 9e before the pouch is filled and can later be opened by simply cutting off the seal 9e. The inlet port 4 is preferably sealed off by applying a short heat seal (not shown) just below the port tube 4 along a line indicated by the arrow 10c.

Figure 2:
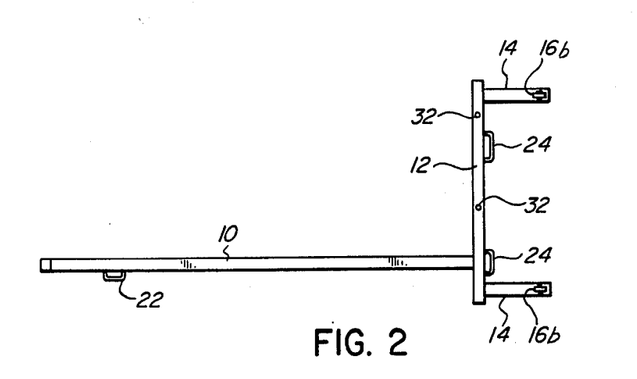
FIG. 2 is a partial cross sectional view taken through a fin on one side of the pouch of FIG. 1 to show how the fin may be laminated by heat sealing along its inner and outer edges.
Figure 3:
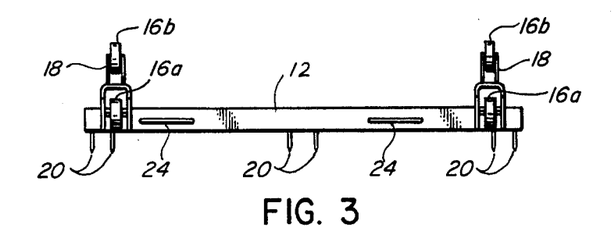
FIGS. 3 and 4 are partial cross-sectional views similar to FIG. 2 but illustrating other embodiments in which the fin is laminated by use of an adhesive.
Figure 4:
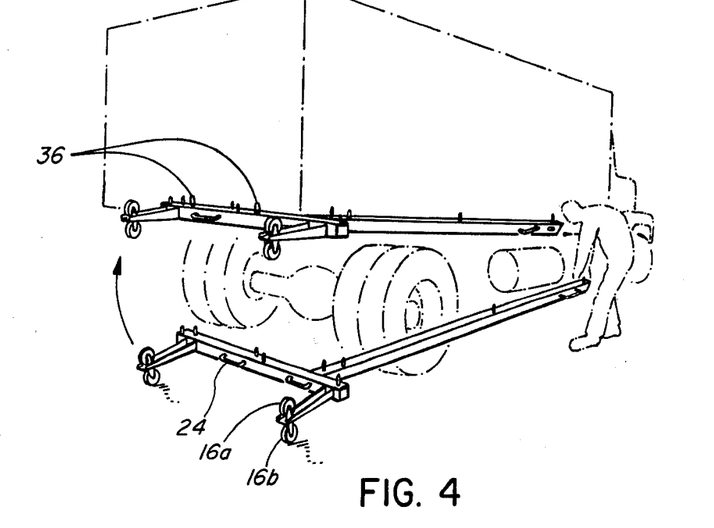

The pouch 1 of the invention contains as a necessary part of its construction the fin supporting means 11 which extend along at least about 15% of the outer peripheral edges of the pouch, preferably at least about 40 to 50% or more, so as to provide extensions of the two film layers which project outwardly from the main body of the pouch substantially beyond the heat-sealed area or region of heat seals 9 which lie adjacent to and define the inner edges of the pouch enclosure 7. In order for these fin extensions 11 to function properly as supporting flaps or holders, they must project outwardly to a distance which measures at least three and preferably at least five times the thickness of the flat pouch when frozen, this distance being measured over the complete laminated fin including the heat sealed portions 9. As shown in FIGS. 2-4, these fins extend outwardly to a distance about four times the thickness of the flat pouch filled with frozen biological liquid 2. Without this minimal extension, the fins do not adequately protect the region of the heat seals 9 surrounding the main body or enclosure 7 of the pouch. Also, the fins 11 need to provide a certain minimal area of high strength and abrasion resistance outside the heat seal region in order to act as supporting means for the pouch.

The two layers of polyethylene film of the pouch 1 as shown in FIGS. 2-4 are held apart by the biological material 2 in liquid or frozen form, but these layers are laminated together in the fin 11a not only by the heat seal 9a but at least in a marginal area adjacent the outermost edge 11' of the fin. In this marginal area, lamination to join both film layer together can be accomplished with another narrow heat seal 12a (FIGS. 1 and 2) or by means of an adhesive 13 (FIG. 3). Alternatively, the entire fin 11a beyond the heat seal 9a can be laminated by the adhesive layer 13b (FIG. 4), using any suitable adhesive for the polyethylene film so as to form a permanent bond, for example: polybutadiene; or a silicone resin in a xylene solvent; or a 2-component polyurethane system. The adhesive layer increases the thickness of the film laminate only slightly, the thickness of this layer 13 being shown much larger than its actual size in FIGS. 3 and 4.

This lamination of the fins 11 not only increases their strength and abrasion resistance but also ensures that the two layers of film remain in close intimate contact when used as supporting members. At least the central and major portion of each fin is preferably maintained in its biaxially oriented state, i.e. without heat sealing or otherwise heat treating the film in this fin member except where essential along its inner and preferably its outer edges.

It will be noted that both the pouch enclosure 7 and the fins 11 in FIG. 1 are substantially completely heat sealed around the entire periphery of the pouch 1. Although this construction is not entirely essential except for initially open edges of the enclosure 7, there is a substantial reduction in the cost of manufacturing these pouches where the required heat seals can be applied in one or at most two operations. Such pouches frequently have been made from a narrow extruded polyolefin tubular film of the exact width or length of the pouch so as to require heat sealing only across the two open ends of the initial tube. The present invention may also utilize such narrow tubular films with the fins exteding only from the heat sealed ends. However, it is less costly to use conventionally blown tubular films of very large diameter, especially to obtain high quality, biaxially oriented film materials, and then heat seal the two separate film layers around the entire pouch as described. In mass production, each pouch can be die cut to exact size after the heat seals have been applied, and the resulting pouch enclosure and attached fins are of a unitary integral structure.

In general the plastic film used to make the pouch should provide a wall thickness of about 3 to 10 mils, using one, two or three plies in each of the two walls so that the fins may contain as many as six plies. Two- or three-ply walls should be adhesive laminated or coextruded so that the pouch enclosure has solid walls free of bubbles or air pockets. In order to improve durability, one can employ different transparent and cryogenically durable film-forming polymers to provide different plies, preferably with at least one ply being the heat-sealable polyolefin such as polyethylene. Other suitable film-forming polymers include Teflon and the highly oriented polyesters. The different plies, if not coextrudable, should be laminated together with an adhesive, for example with the polyolefin ply as the inner facing surface of the pouch and the other ply, e.g. Teflon, being adhered thereto as the outer facing surface of the pouch.

If desired, one or more fins can contain at least one hang-up hole 14, i.e. a circular opening enclosed by a heat seal 15 and positioned in the fin so that the pouch can be hung on a suitable engaging hook in the optimum position for removal of all of the thawed liquid through the outlet port 4 at one corner of the pouch. One advantage of a slack filled plastic pouch is that one can fill it through inlet port 3 under sterile conditions while the outlet port 4 remains sealed as at 9e, and likewise the pouch can be emptied through the outlet port 4 after removing seal 9e while the pouch is sealed off from the inlet port 3 by the heat seal applied as indicated by the arrow 10c, i.e. a heat seal connecting 12a with 9a. Thus, it is unnecessary to expel air or other gas from the pouch when being filled with a liquid, and the pouch can be gravity drained without introducing air into the pouch. Sterile conditions are thus maintained at all times.

Figure 5:
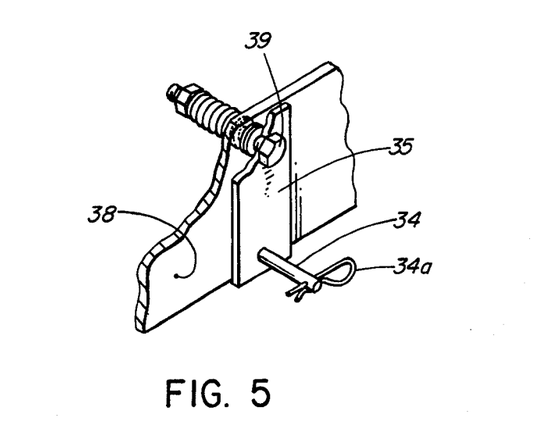
FIG. 5 is a partly schematic cross sectional view taken transversely through one side of the pouch of FIG. 1 as it is clamped between two metal plates having edge closure and clamping means to grip and hold the pouch in place.

The use of the fins 11 as a supporting means for the pouch 7 is illustrated in partly schematic form by the embodiment shown in FIG. 5, using the fin in which the two film layers are laminated only by heat sealing at 9c and 12c as indicated in FIGS. 1 and 2. The pouch 7 filled with frozen liquid 2 is contained between the two parallel aluminum plates 16 and 17 with their respective flanges 18 and 19 formed at right angles to the plates and partly forming edge closures around the periphery of the two plates. In order to adapt the edge closures to any given thickness of film in the laminated fins, a pair of opposing elastomeric shims 20 and 21 are removably mounted on flanges 18 and 19 so as to gently but firmly press against the fin 11a to hold it in place. By using a tongue 22 and groove 23 construction, the fin 11a is more securely held when plates 16 and 17 are clamped in place with spring clamping means 24 and 25 as indicated by the force direction of the two arrows. The fin 11a is folded up and over the upper plate 16 and held flat against the plate by the spring clamp element 25. It will be noted that the shims 20 and 21 act not only to form part of the edge closure but also have a positive clamping or gripping effect. These shims can be made of any material which will resist cryogenic temperatures and remain fastened to the flanges of the metal plates, if necessary by means of removable screws or the like (not shown).

The embodiment of FIG. 5 has the advantage that the fin 11a runs from the heat seal 9c to the flanges and their clamping shims 20 and 21 in a plane at the midpoint of the thickness of pouch 7 and parallel to retaining plates 16 and 17. There is practically no distortion of the pouch 7 or heat seal area 9c, and any sudden shock or jolt produced for example by dropping the unit on its edge will be transmitted to the relatively strong central portion of the fin 11a between the two heat seals 9c and 12c. These specific edge closure means and clamping means are preferably arranged on two, three or even four sides of the enclosure formed by the two flanged metal plates 16 and 17.

Figures 5, 6, 6A, 6B:
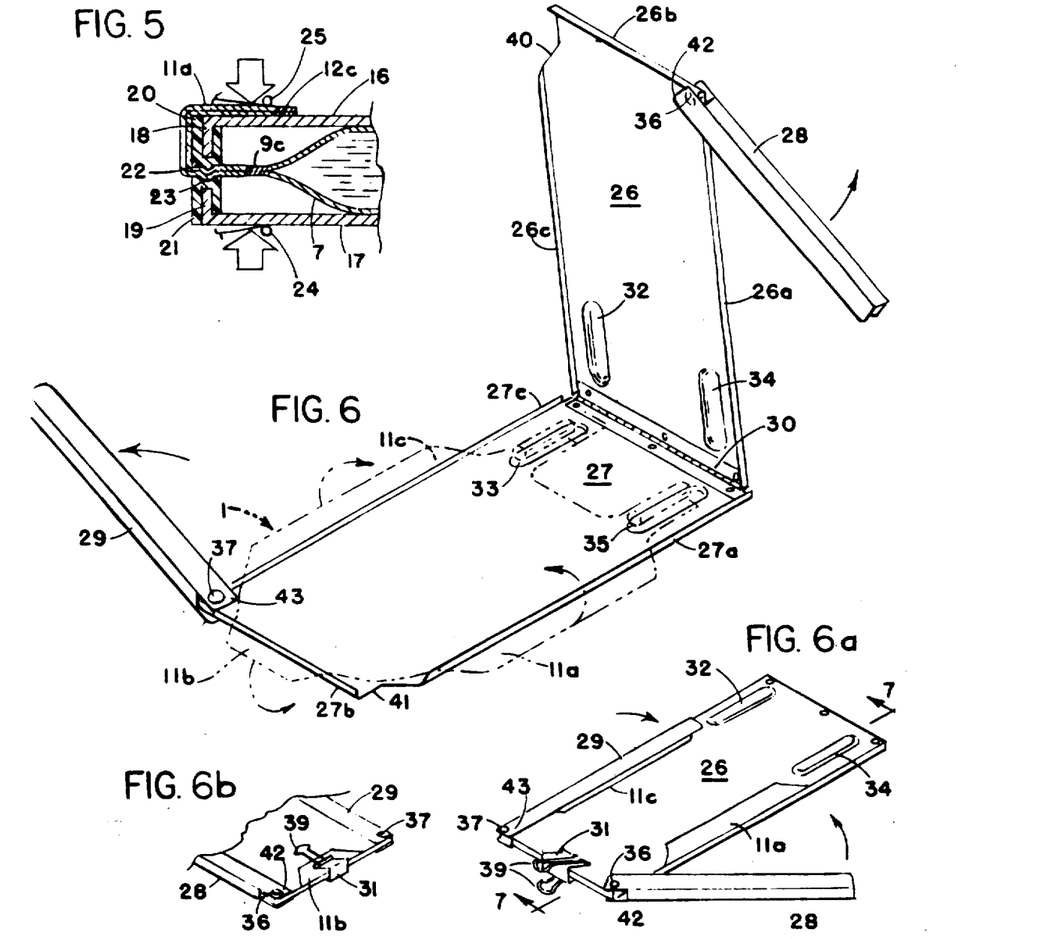
FIG. 6 is a perspective view of an especially preferred embodiment of the metal container according to the invention, shown in its open position and with the pouch of FIG. 1 indicated in phantom lines.
FIG. 6a is a perspective view, reduced in size, of the metal container of FIG. 6 after it has been closed with the pouch partly clamped in place to provide a complete package assembly.
FIG. 6b is a partial perspective view of the closed metal container of FIG. 6a which has been turned over to illustrate the opposite side with one supporting fin clamped in place.

In FIG. 6 there is illustrated an especially preferred embodiment of the package for cryogenically frozen liquids according to the invention, combining the pouch 1 of FIG. 1 with a special rectangular metal enclosure which includes two substantially planar metal retaining plates 26 and 27 having edge closure means at both ends and along both sides so as to completely enclose and protect the pouch 1, shown in phantom lines with arrows indicating the direction in which the fins of the pouch are to be folded around the metal plates. The metal enclosure in this case is designed with two supporting arms 28 and 29, in the form of U-shaped channel members, each arm being pivotally mounted at one end to the upper plate 26 and the lower plate 27, respectively. Hinge means, preferably a piano hinge 30, provides the edge closure at one end while permitting the plates 26 and 27 to swing from an open position as shown in FIG. 6 to a closed position where their inner opposing surfaces are spaced narrowly apart in substantially parallel relationship. The details of this preferred combination are shown in greater detail in FIGS. 6a, 6b, 6c and 7, to explain the clamping function of the swinging arms or channel members 28 and 29, supplemented by at least one steel spring binder clamp 31.

Two sets of opposing concave depressions or grooves 32,33 and 34, 35 are formed in the inner facing surfaces of plates 26 and 27 as means to receive the port tubes 3 and 4 which preferably have an outer diameter which is slightly greater than the thickness of the frozen pouch 1. These larger port tubes permit better access to the pouch enclosure and are more adaptable to different fittings. The ports are thus fully enclosed with the rest of the pouch inside the metal plates without disturbing the uniform thickness of the frozen liquid.

Figure 6C:
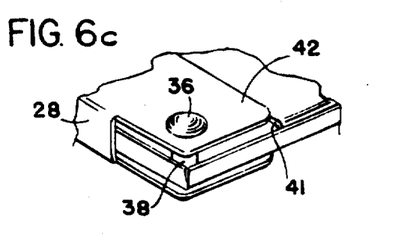
FIG. 6c is an enlarged partial view taken from one corner of the metal container of FIG. 6b to better illustrate the closed construction at the clamp pivot point.

The two channel arms 28 and 29 are pivotally mounted by suitable pins or posts 36 and 37, respectively, in the form of a bolt or rivet fastened to the arm itself and passing through an opening in the metal plate 26 or 27, preferably with a sleeve bearing 38 as shown in FIG. 6c to act as a spacer and support for the freely swinging arm. By mounting the pivotable arms at the end of the container opposite the hinge 30, and on opposite corners of the two metal plates 26 and 27, these arms can be swung to an open position as indicated by the arrows in FIG. 6 and used as handles to open the package for insertion or removal of the pouch 1. When the package is frozen, the arms offer a means of readily separating the two plates and/or transporting the package with minimum discomfort, since the arms will quickly reach room temperature after being swung away from the frozen package. The spring binder clip 31 is sufficient to hold plates 26 and 27 together while arms 28 and 29 are being used as handles.

Figure 7:
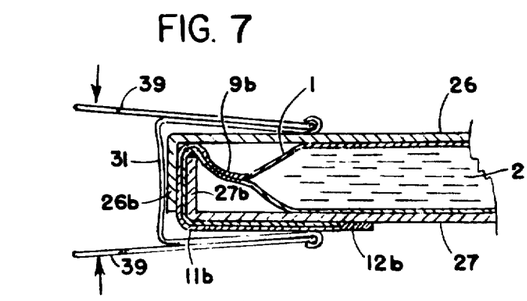
FIG. 7 is a partial and enlarged cross sectional view taken on line 7—7 of FIG. 6a to illustrate the use of a spring clamp to hold the fin in place.

The wire handles 39 of these spring clips swing open in conventional manner to act as leverage arms as shown by the arrows in FIG. 7 in order to open and close the clip. Once the clip 31 is fastened, the wire handles are folded over flat against the plate 27 as shown in FIG. 6b. Such wire handles are designed to be removed from the spring clips if desired during long periods of storage. Spring clips of this kind are readily available in different sizes as well known binders for thick stacks of paper.

Each of the metal plates 26 and 27 has a cut-out or notch 40 and 41 at the same end which carries the channel arm 28 or 29 but at the other corner so as to provide clearance for the overlapping ends 42 or 43 of each channel arm when in its open position. As the arms 28 and 29 are swung to a closed position (FIG. 6a), the ends 42 and 43 pass over one edge of each notch 40 and 41 so as to lightly lock the two plates together even before the arms are fully closed. When the channel arms are completely closed as in FIGS. 6b and 6c, the open area of the notch 41 is substantially completely closed by the end piece 42. The channel arms 28 and 29 thus serve as protective closure means in addition to their clamping or gripping function.

In FIG. 7, the spring clip 31 clamps the plates 26 and 27 together at the end of the container which will swing open, viewed as a partial cross section taken on line 7—7 of FIG. 6a, to illustrate the manner in which the pouch 1 is placed within the metal enclosure with its fins folded out and around one of the plates 26 or 27. Again, the pouch 1 as shown in FIGS. 1 and 2 is used by way of example, the two layers of the main pouch 7 being heat sealed at 9b and 12b to provide a laminated fin member 11b.

Each of the plates 26 and 27 has a flange 26b and 27b, respectively, as a closure member perpendicular to the plate and offset sufficiently from one another to snugly receive the fin 11b as it is folded over the lip of the inner flange 27b, then down between this inner flange and the outer flange 26b and finally stretched flat on the outer lower surface of plate 27. The pouch and fins are held in place primarily by the spring clip 31, but the flanges 26b and 27b are preferably constructed and arranged to also assist in firmly gripping the fin members and holding the pouch in place. Likewise, as the arm clamps 28 and 29 are closed over the side edges of the metal container, they press fit over their respective fin members to further support and hold the pouch in a fixed position.

The flanges around three sides of each of the plates 26 and 27 are shown in FIG. 6, and the two sets of side flanges 26a,27a and 26c,27c function in the same manner as the flanges 26b,27b shown in detail in FIG. 7, except that they overlap one another in the opposite direction, i.e. so that the flanges 26a and 26c face the inner side of the container while the flanges 27a and 27c face the outer side of the container. And the fin members 11a and 11c fold up over the upper plate 26 (see FIGS. 6 and 6a) while the other fin member 11b folds down under the lower plate 27 (see FIGS. 6b and 7).

When constructed in this preferred manner, the metal container of the invention is relatively inexpensive to manufacture, but fully protects the frozen pouch against ruptured neat seals, accidental punctures or other mishandling during its processing, storage and subsequent use of the biological liquid.

Pouches having essentially the same construction as that shown in FIGS. 1–4 combined with the metal container of FIG. 6 have been tested over an extended period of time, and it has been found that accidental ruptures or other damage are practically completely eliminated. At the same time, the invention permits a very thin uniform cross section of the liquid contained in the slack filled pouch 1, so that rapid freezing can take place at cryogenic temperatures and at a rate which ensures the quality of the frozen material. Since the typical thickness of this frozen cross section is about 2 to 10 millimeters, it will be apparent that substantially flat and parallel metal plates offer the best results while also avoiding deformations caused by folding the pouch or by interference from port members.

In order to provide a sample to be used as a control during the freezing operation, a special test package has been developed which requires only a slight modification of the metal container and the slack filled pouch as shown in detail in FIGS. 8 through 11 on the third sheet of drawings. In this instance, the two metal retaining plates 44 and 45 are provided with a hinge 46 at one end which preferably has all four corners cut away along the dotted lines in order to provide free access to port members (see FIGS. 8 and 9). The end opposite the hinge 46 has cooperating flanges 44b and 45b which correspond exactly to the flanges 26b and 27b in FIG. 7 and perform the same function. There are no flanges as closure means along the side edges of the container of FIG. 8, and the fin members 11a and 11c are clamped and held securely in place only by the additional spring clips 31, preferably at least two per side. The clamping action of these spring clips 31 is schematically shown in FIG. 8a. The open sides and end closure of flanges 44b and 45b are further shown in enlarged detail in FIG. 8b.

Figures 8, 8B:
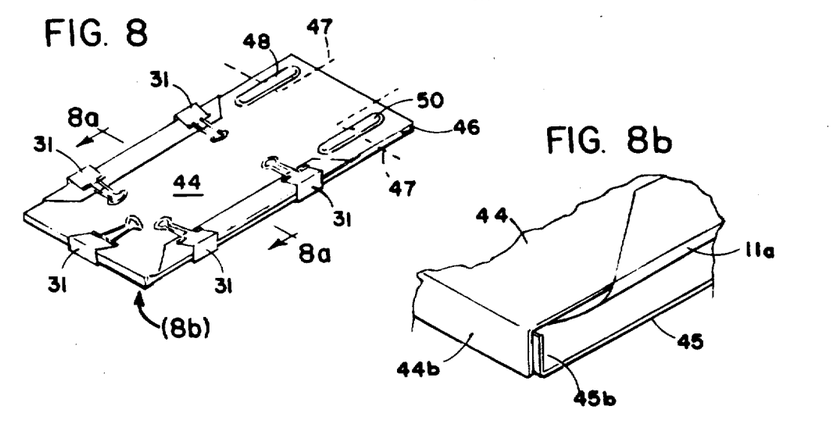
FIG. 8 is a perspective view of another embodiment of the package assembly of the invention which is especially useful as a sample control package.
FIG. 8b is an enlarged partial view taken from one corner of the metal container of FIG. 8a to better illustrate the package of FIG. 8.
Figure 8A:
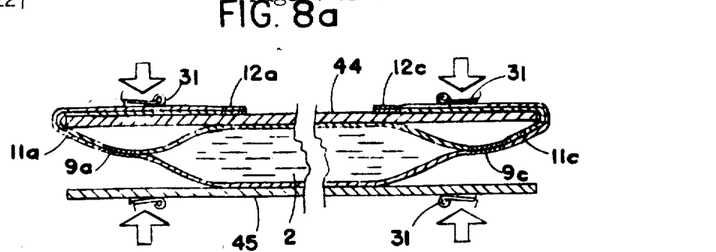
FIG. 8a is a cross sectional view taken on line 8a—8a of FIG. 8.

The embodiment illustrated by FIGS. 8, 8a and 8b represents the most economical metal container for general use in accordance with the invention, and it has the advantage of providing a clear view of the pouch and its contents through the open sides. Also, very inexpensive spring clips 31 perform the primary clamping function and, aside from the hinged closure at one end and the flange closures at the other end, the flat metal plates 44 and 45 require only the concave grooves in pairs 48, 49 and 50, 51 to hold the port means of the pouch. On the other hand this more open structure with a view of the pouch does not offer adequate protection for a frozen pouch which must be used to preserve valuable biological material. At best, such open sided packages should be used only temporarily during freezing while using a separate enclosed container for storage purposes, even at the risk of a separate handling step.

Figure 9:
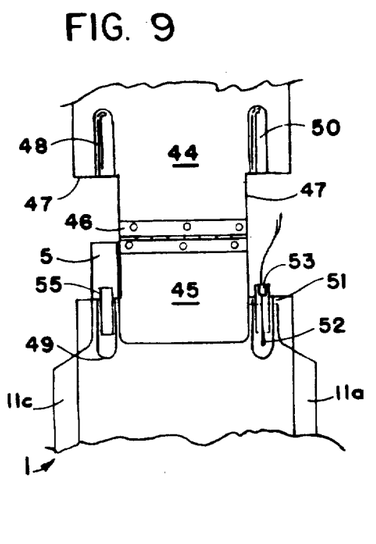
FIG. 9 is a partial front elevational view of the upper end of the control package of FIG. 8 with exposed port means, the package being vertically positioned and the face cover of the metal container being hinged completely open to a vertical position.
Figure 10:
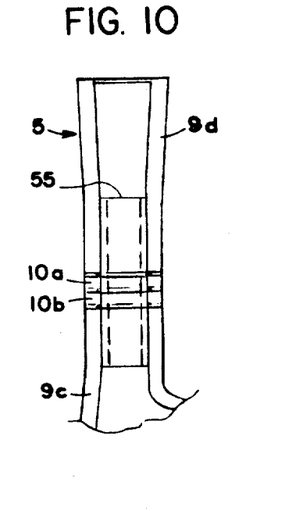
FIG. 10 is an enlarged partial view of the upper left port means of FIG. 9.
Figure 11:
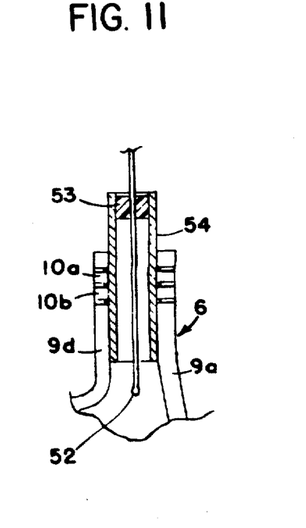
FIG. 11 is an enlarged partial cross sectional view of the upper right port means of FIG. 9.

Because it is not so important to preserve the biological material in a test package, the simplified container and clamping system of FIGS. 8 through 9 are particularly useful as a means of observing the contents of the transparent pouch while monitoring temperature conditions by inserting a temperature sensing means such as a thermocouple 52 through a self-sealing rubber stopper 53 in one of the ports 54. The other port 55 can serve as an outlet port or as a means of withdrawing a small portion of liquid material as a sample during the freezing process. These ports are illustrated in detail by the enlarged views of FIGS. 10 and 11, the pouch 1 with its flanges 11 and heat seals 9 along the tubular segments 5 and 6 being essentially the same as in FIG. 1. By using the slightly oversized port tube 54, the point of the thermocouple 52 which is temperature sensitive can be very carefully located in the middle of the pouch cross section, i.e. so as to measure the temperature at a point midway between the enclosing pouch surfaces where freezing is last to occur. The thermocouple can be continuously monitored so as to have a complete read out or printed record of the freezing process. The same conditions can be expected to prevail in all of the other packages being frozen in the same batch with this test sample.

The foregoing description is directed to certain preferred embodiments of the invention by way of illustration, and the invention is not to be limited to these embodiments. While the invention is primarily concerned with the complete package of cryogenically frozen biological liquid material, the individual components such as the pouch and metal container are well adapted to special designs to serve special functions. The appended claims are to be considered in this context so as to properly define the scope of the invention.

I claim:

1. A package for a cryogenically frozen liquid material comprising:
   a normally flexible, slack-fillable, enclosed, flat plastic pouch formed by two layers of a cryogenically durable, transparent, thermoplastic polymer film which is heat-sealed to define inner edges of the pouch enclosure; and
   laminated fins extending along at least about 15% of the outer peripheral edges of the pouch, said fins being extensions of said two layers of film which project outwardly beyond the heat-sealed area adjacent said inner edges of the pouch enclosure, said fins being laminated together along their inner edges by said heat-sealed area and also at least in a marginal area adjacent to their outermost peripheral edges.

2. A package as claimed in claim 1 wherein said fin extensions project outwardly to a distance which measures at least three times the thickness of the flat pouch when frozen.

3. A package as claimed in claim 1 wherein said fin extensions project outwardly to a distance which measures at least five times the thickness of the flat pouch when frozen.

4. A package as claimed in claim 1 wherein the pouch is composed of a cryogenically durable, biaxially oriented polyolefin film.

5. A package as claimed in claim 4 wherein the polyolefin consists essentially of polyethylene.

6. A package as claimed in claim 2 wherein the film layers of the pouch include at least one ply of a cryogenically durable, biaxially oriented polyolefin film.

7. A package as claimed in claim 6 wherein the polyolefin consists essentially of polyethylene.

8. A package as claimed in claim 1 wherein the pouch is substantially rectangular in shape with fins on at least two opposite sides.

9. A package as claimed in claim 8 wherein the fins are located on three sides of the pouch with sealable inlet and outlet port means arranged on the remaining fourth side of the pouch, said fins being cut away at an angle to the corners of the pouch to provide substantially trapezoidal supporting means.

10. A package as claimed in claim 1 wherein the film layers of the fins are laminated together at least in said marginal area by an adhesive.

11. A package for a cryogenically frozen liquid material comprising in combination:
    a metal enclosure including two substantially planar metal retaining plates which are closable to a position in which their inner opposing surfaces are spaced narrowly apart in substantially parallel relationship;
    a flat plastic pouch composed of an oriented, cryogenically durable, thermoplastic polymer film, said pouch being sealed around its peripheral edges in order to be slack filled with a liquid while fitting within the confines of said metal retaining plates in their closed position;
    at least one fin member attached securely to a peripheral edge of said pouch and extending outwardly of the pouch and said retaining plates; and
    clamping means to fasten said at least one fin member to said metal retaining plates so as to hold said pouch in a substantially fixed position between the plates.

12. A package as claimed in claim 11 wherein said clamping means includes at least one spring steel binder clip which grips said at least one fin member when folded over in place against an outer surface of one of said metal retaining plates.

13. A package as claimed in claim 12 wherein said metal enclosure is substantially rectangular in shape with edge closure means at two opposing ends thereof while remaining open along the remaining two opposing side edges to permit viewing the enclosed pouch.

14. A package as claimed in claim 13 wherein said pouch is substantially rectangular in shape with fins on at least two opposing sides, and a plurality of spring steel binder clips to grip each of said fin members when folded over in place.

15. A package as claimed in claim 13 wherein the fin members are located on three sides of the pouch with two tubular ports on the fourth side of the pouch adjacent the corners thereof, one of said ports being a liquid inlet port an the other port having a stopper which permits the insertion of a temperature sensing means, and wherein the corners of said metal enclosure are cut away to provide access to said ports while the pouch is fastened by said clamping means.

16. A package as claimed in claim 11 wherein said metal enclosure is substantially rectangular in shape with edge closure means at two opposing ends thereof and also along the two opposing sides thereof.

17. A package as claimed in claim 16 wherein said clamping means include a pair of channel arm clamps, each clamp sliding over one of the opposing sides of the metal enclosure to a closed position bracketing said metal retaining plates with a fin member folded therebetween and each clamp being pivotally mounted at one end to a corner of said metal enclosure to swing from said closed position to an open position permitting the metal plates to be opened.

18. A package as claimed in claim 17 wherein said metal retaining plates are hinged at one end and each has one of said channel arm clamps mounted thereto at its other end, so that the metal plates can be swung open or closed by manipulation of said arm clamps in their open position.

19. A protective supporting package to enclose a flexible plastic film pouch adapted to contain a cryogenically frozen liquid material, said package comprising:

two substantially rectangular metal plates with hinge means at one end to permit the plates to swing from an open position to a closed position in which their inner opposing surfaces are spaced narrowly apart in substantially parallel position, said metal plates further including edge closure means at the other end opposite the hinged end and also including edge closure means along the two opposing sides to substantially completely enclose said pouch when said plates are in their closed position; and a pair of supporting arms, one arm being pivotally mounted to the right corner of one plate at the end opposite the hinged end and the other arm being pivotally mounted to the left corner of the other plate at said end opposite the hinged end, as viewed facing the end opposite the hinged end.

20. A protective supporting package as claimed in claim 19 wherein said supporting arms are U-shaped channel members with their sides sliding over the outer surfaces of said metal plates along the two opposing sides thereof to snugly clamp the plates together when a plastic film layer of said pouch is folded and held between an outer plate surface and the inner surface of one side of the channel member.

* * * * *

UNITED STATES PATENT AND TRADEMARK OFFICE
CERTIFICATE OF CORRECTION

PATENT NO. : 4,469,227                     Page 1 of 4

DATED : September 4, 1984

INVENTOR(S) : Clifford Faust

It is certified that error appears in the above-identified patent and that said Letters Patent is hereby corrected as shown below:

IN THE DRAWINGS:

Please substitute the following three (3) sheets of drawings to replace the erroneous two (2) sheets of drawings from Patent No. 4,469,277, an obvious error. This Certificate to apply to the Grant only.

Signed and Sealed this

Sixth Day of May 1986

[SEAL]

Attest:

DONALD J. QUIGG

Attesting Officer    Commissioner of Patents and Trademarks

Patent No. 4,469,227

Patent No. 4,469,227